(12) United States Patent
Bryan et al.

(10) Patent No.: US 7,090,185 B2
(45) Date of Patent: Aug. 15, 2006

(54) DEVICE FOR SUPPORTING A MEDICAL APPARATUS

(76) Inventors: Judith Lynn Bryan, 15006 One-O-One Trail, Amarillo, TX (US) 79116; Wanda Morgan White, 2407 SE. 19th Ave., Amarillo, TX (US) 79103

( * ) Notice: Subject to any disclaimer, the term of this patent is extended or adjusted under 35 U.S.C. 154(b) by 0 days.

(21) Appl. No.: 10/827,212

(22) Filed: Apr. 19, 2004

(65) Prior Publication Data

US 2005/0230580 A1    Oct. 20, 2005

(51) Int. Cl.
*A47D 15/00* (2006.01)
(52) U.S. Cl. ........................ 248/323; 248/317
(58) Field of Classification Search ................ 248/540, 248/541, 251, 520, 514, 534, 538; 160/345; 5/503.1, 658
See application file for complete search history.

(56) References Cited

U.S. PATENT DOCUMENTS

| | | | | |
|---|---|---|---|---|
| 602,055 A * | 4/1898 | Campbell | ............. | 248/231.71 |
| 2,711,872 A * | 6/1955 | Lampke | ....................... | 248/103 |
| 3,929,309 A * | 12/1975 | De Vore | ..................... | 248/118 |
| 4,524,475 A * | 6/1985 | Valentino | .................... | 5/507.1 |
| 4,735,388 A * | 4/1988 | Marks | ........................ | 248/103 |
| 4,834,097 A * | 5/1989 | Phillips et al. | .............. | 606/148 |
| 4,875,651 A * | 10/1989 | Wergin et al. | ........... | 248/291.1 |
| 5,489,075 A * | 2/1996 | Ible | ............. | 248/104 |
| 5,645,335 A * | 7/1997 | Brunner et al. | ............. | 353/122 |
| 5,775,654 A * | 7/1998 | Price | ..................... | 248/231.61 |
| 6,039,293 A * | 3/2000 | Minet | ....................... | 248/125.8 |
| 6,598,837 B1 * | 7/2003 | Howard et al. | ............. | 248/103 |
| 6,817,046 B1 * | 11/2004 | Srour et al. | .................. | 5/99.1 |

* cited by examiner

*Primary Examiner*—Kimberly Wood
*Assistant Examiner*—Steven Marsh
(74) *Attorney, Agent, or Firm*—McKee, Voorhees & Sease, P.L.C.

(57) ABSTRACT

A device is provided to support a medical element over a bed. The device includes a base mountable to the bed, a clamp to hold the medical element, and a rod between the base and the clamp to support the element over the bed. The rod is connected to the base with a universal joint to permit movement of the medical element between use and non-use positions. The rod is adjustable.

9 Claims, 4 Drawing Sheets

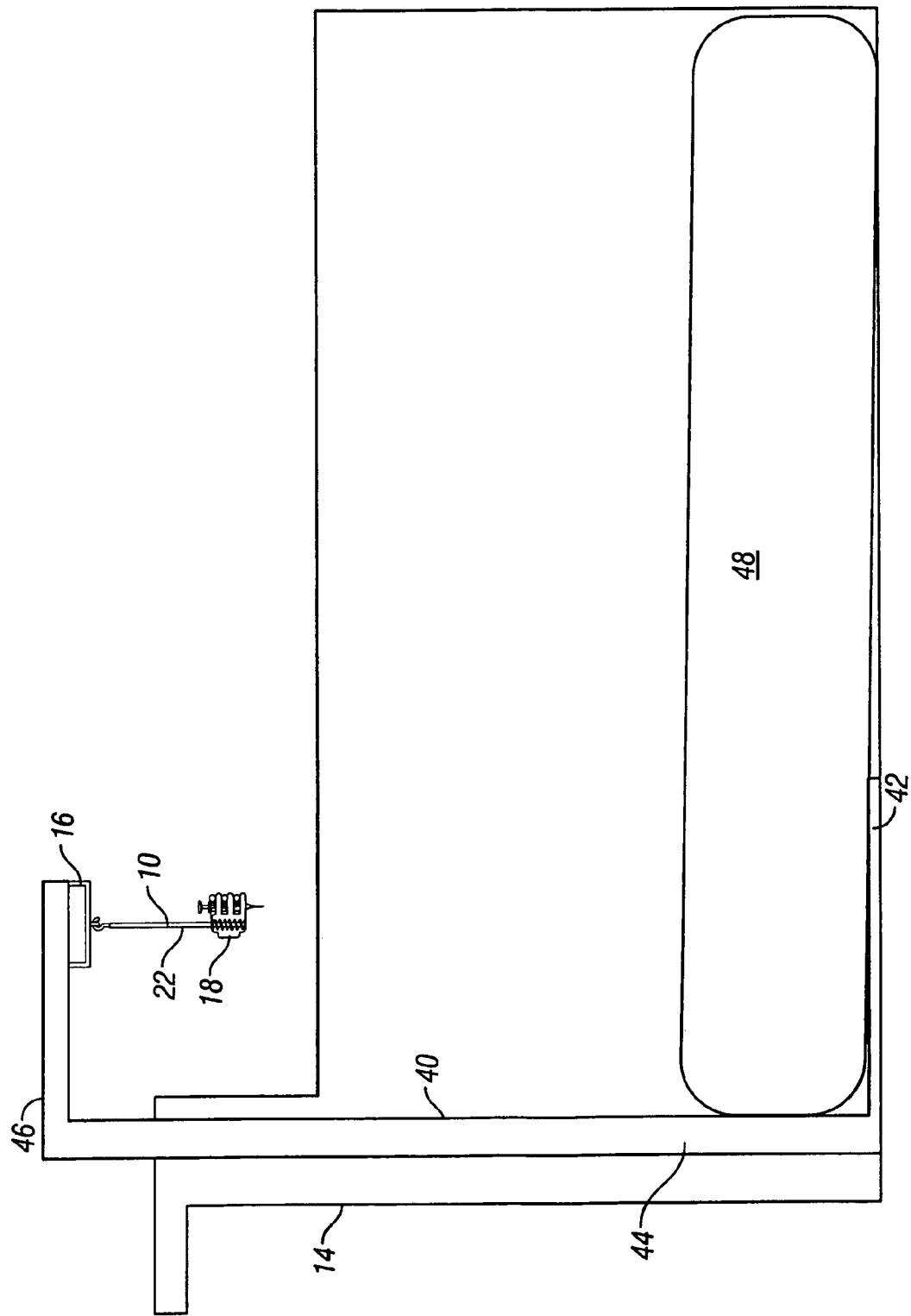

DEVICE FOR SUPPORTING A MEDICAL APPARATUS

BACKGROUND OF THE INVENTION

Patients in hospital beds, nursing home beds, or other treatment beds often require medical apparatus for introducing or removing fluids from the body. The apparatus typically includes a syringe, tubing and other elements which are positioned close to the patient.

For example, the use of syringes for stomach decompression and for the feeding of infants is a common medical procedure. When providing care to premature infants, normal infants, or any other patient, the precise application of feeding material or other activity ideally requires that the syringe, tubing, conduits, or other medical apparatus to the patient operate undisturbed and unimpeded. Furthermore, because syringes or other medical apparatus' are of different sizes and employ different capacities, the weight of the medical apparatus' employed varies. The tubing or conduits connecting the apparatus to the patient is frequently attached by medical tape or elastic bands. Unfortunately, because radiant warmers are commonly employed to keep a patient warm, the same heat that warms the patient compromises the adhesive qualities of the tape and elastic bands, as well as presenting a separate safety hazard to the patient.

Three problems which frequently arise pertain to: (1) the inadvertent disconnection or interruption of flow of the medical dispensing or accumulating devices with the patient; (2) the hazard posed to the patient from having an apparatus fall against or contact a patient being treated; and, (3) uneven flow of material either into or out of the medical apparatus in the course of operation depending upon the relative position of the apparatus and the patient.

Currently available apparatus' and methods do not satisfactorily address these common problems. Current practice involves the use of tape or rubber bands to hold the medical apparatus, such as the syringe, or the tubes, or the container for the formula being dispensed. However, when a patient moves, the apparatus may be displaced or disconnected. In the case of an infant, it is frequently the case that the frequent movement of the child-patient causes the apparatus' (namely syringes) to be disturbed and the flow of feeding formula to be interrupted. Additionally, the capacity of the tape or rubber bands is frequently exceeded by the weight of the formula being dispensed. With respect to feeding material, it is frequently desirable to have the feeding formula elevated over the patient; open top cribs make such feedings problematic, and without adequate support, poses a danger to the patient. In the context of stomach decompression, it is commonplace for the movement of the patient to cause leakage or spillage of gastric contents being tubally removed from the patient.

Accordingly, a primary objective of the present invention is the provision of a device for supporting a medical apparatus over a bed.

Another objective of the present invention is the provision of a syringe assembly support device which maintains the syringe assembly in a safe, yet functional position for use with a patient in a bed.

A further objective of the present invention is the provision of a support device for a syringe assembly which is adjustably positioned on a bed.

Still another objective of the present invention is the provision of a support device for a medical apparatus which is pivotally connected to the bed for movement between use and non-use positions.

A further objective of the present invention is the provision of a support device for medical apparatus which can be secured beneath a mattress and extend above the mattress to position the apparatus over the mattress.

Yet another objective of the present invention is the provision of a support device for a medical apparatus which can be quickly and easily mounted on a bed and to which a medical apparatus can be quickly and easily connected.

These and other objectives will become apparent from the following description of the invention.

SUMMARY OF THE INVENTION

The syringe assembly support device of the present invention is particularly suited for use on a crib or bed to support a medical apparatus, such as a syringe assembly, above the mattress and out of reach of the baby or patient in the crib or bed. The device includes a base mountable to the crib or bed, a clamp to hold the apparatus, and a rod extending between the base and the clamp to support the apparatus above the crib or the bed. The base may be slidably or pivotally mounted to the bed. The rod may be length adjustable. The rod is pivotally connected to the bed so that the medical apparatus may be moved between a use and non-use position.

BRIEF DESCRIPTION OF THE DRAWINGS

FIG. 5 is an elevation view showing a member extending from beneath the mattress for positioning the device over the mattress.

DETAILED DESCRIPTION OF THE PREFERRED EMBODIMENT

Figure 1:
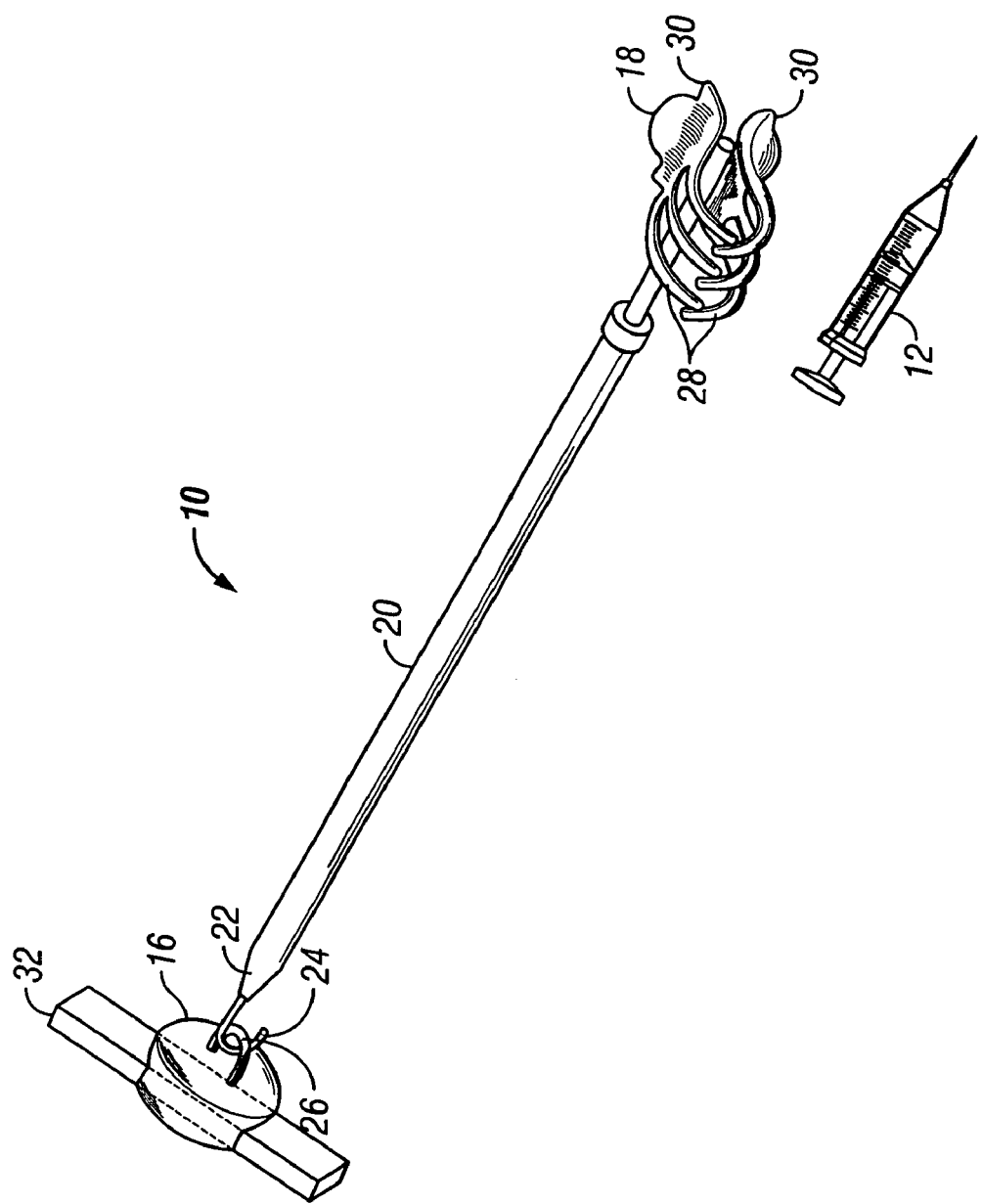
FIG. 1 is a perspective view of the support device of the present invention shown supporting a syringe assembly and having an extensible rod.
Figure 2:
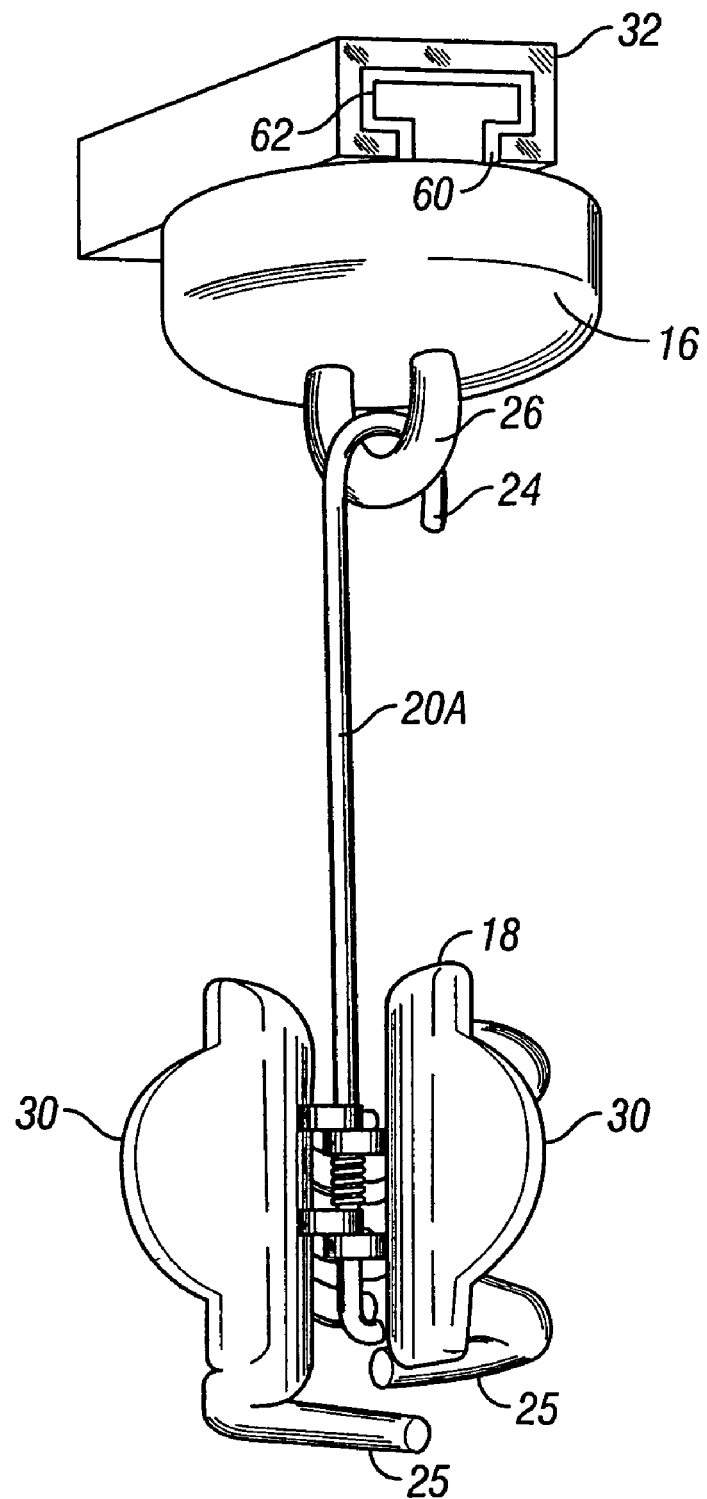
FIG. 2 is a perspective view showing another embodiment of the support device with a non-extensible rod.

The support device of the present invention is generally designated by the reference numeral 10 and is intended for use to support a medical element 12, such as a syringe, above a bed 14. The support device 10 includes a base 16, a clamp 18, and a rod 20 extending between the base 16 and the clamp 18. The rod 20 may be extensible or telescoping so as to have an adjustable length, as shown in FIG. 1. Alternatively a non-extensible rod 20A may be provided, as shown in FIG. 2.

Preferably, the connection between the rod 20, 20A and the base 16 defines a universal pivot joint so that the rod is pivotal and rotatable relative to the base 16. For example, as seen in FIGS. 1 and 2, first end 22 of the rod 20, 20A includes a hook 24 adapted to be received within an eye 26 of the base 16. Alternatively, a ball joint may be provided between the base 16 and the rod 20.

The clamp 18 may take numerous forms. For example, as seen in FIGS. 1 and 2, the clamp 18 includes opposing fingers 28 which are normally biased to a closed position by a spring 29 to hold the medical element 12. The fingers 28 may be moved to an open position simply by a person squeezing the hands 30 of the clamp 18 opposite the fingers 28. A clip or strap may be provided on the bar 32 to hold the rod 20 and clamp 18 in a substantially horizontal non-use position, as pivoted from the substantially vertical use position shown in FIG. 3.

Figure 3:
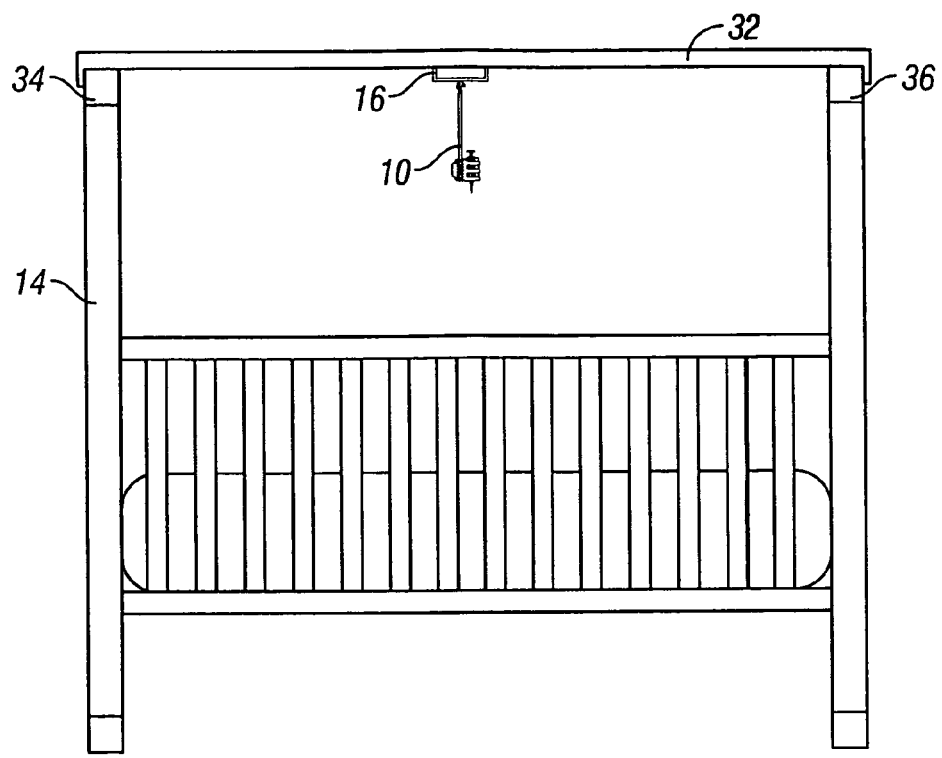
FIG. 3 is an elevation view showing the device mounted on a crib.

The device 10 may be mounted to or supported above the bed 14 in numerous manners. In one embodiment, as shown in FIG. 3, the base 16 is connected to a bar or frame 32 extending between the opposite ends 34, 36 of the bed 14. The base 16 may be adhered to the bar 32. Alternatively, the base 16 may be slidably mounted to the bar 32 so that the device 10 can be moved along the length of the bed 14. For example, the bar 32 may include a slot 60 in the lower surface, and the base 16 may include a tab 62, hook or other member for slidably receipt in the slot. Alternatively, base 16 may extend around the bar 32 for sliding movement there along. The bar 32 may be extensible or telescoping so as to have an adjustable length to accommodate various length beds 14.

Figure 4:
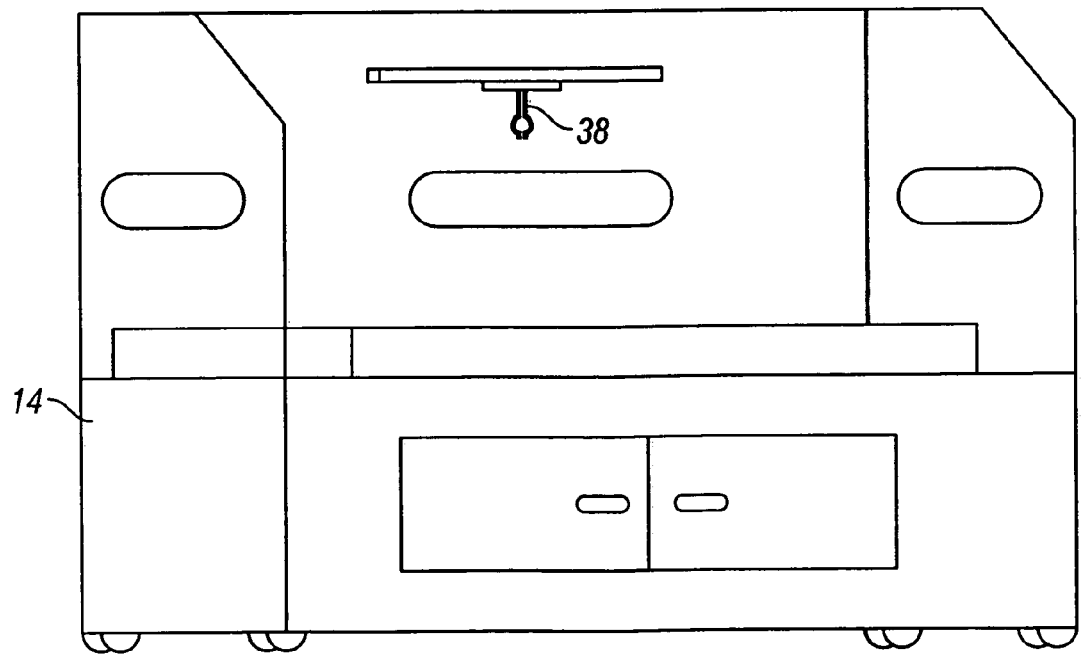
FIG. 4 is an elevation view showing a clip on a hospital isolette for holding the device.

In FIG. 4, a clip 38 is provided on the bed so that the device 10 can be held in a non-used position. Generally, the non-use position of the device 10 is substantially horizontally oriented, though other non-use orientations are contemplated. As an alternative to the clip 38, a hook and loop strap can be used to secure the device 10 in a non-use position.

As an alternative to the bar 32, particularly for use in a bed 14 which does not have ends for supporting the bar 32, a member 40 may be used for supporting the device 10 above the bed 14, as seen in FIG. 5. More particularly, the member 40 includes a foot 42, a leg 44, and an arm 46. The foot 42 is adapted to fit beneath the mattress 48 of the bed 14. The leg 44 extends upwardly, with the upper arm 46 extending substantially horizontally over the mattress 48. The base 16 of the device 10 is connected to the arm 46 in any convenient manner, including a slidable mounting similar to that discussed above with respect to bar 32.

It is understood that the device 10 of the present invention can be used with any type of bed, including a crib, isolette, or radiant warmer used at a hospital for newborn babies. While the device 10 is preferably made of plastic, other materials may be used, including metal or wood. The clamp 18 may be removable from the rod 20 for sanitation or sterilization purposes.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A medical tool support device, comprising:
    a base slidably mountable to a bed with a tab which slides within a slot;
    an articulated clamp for holding the tool; and
    a rod having a first end connected to the base and a second end connected to the clamp, wherein the rod is connected to the base by a hook and eye.

2. The device of claim 1 wherein the rod is pivotal between the operative and inoperative positions.

3. The device of claim 1 wherein the rod is telescopically extensible.

4. The device of claim 1 wherein the base is adhered to the bed.

5. The device of claim 1 further comprising a bar connected to the bed to slidably support the base.

6. The device of claim 1 further comprising a member having a foot adapted to fit beneath a mattress on the bed, a leg extending upwardly from the foot and an arm extending outwardly from the leg to support the base and thereby position the medical element over the mattress.

7. The device of claim 1 wherein the rod is rigid.

8. The device of claim 1 wherein the rod is moveable between a substantially vertical position and a substantially horizontal position.

9. A device for holding a syringe above a bed, comprising:
    a base operatively connected above a bed;
    an extendable rod having two ends with a first end connected to the base, wherein the rod is connected to the base by a hook and eye and
    an articulating clamp incorporated onto a second end of the rod, wherein the clamp has two halves, which articulate around the second end of the rod for holding the syringe and the clamp being normally biased with a spring for holding the two halves of the clamp in a closed position, the two halves have multiple overlapping fingers which can be opened for holding the syringe.

\* \* \* \* \*